United States Patent [19]

Kawakami et al.

[11] Patent Number: 5,200,331

[45] Date of Patent: Apr. 6, 1993

[54] METHOD OF PRODUCING AN AMIDE UTILIZING A MICROORGANISM

[75] Inventors: Kiyoshi Kawakami; Toyozi Tanabe; Osamu Nagano, all of Yokohama, Japan

[73] Assignee: Asahi Kasei Kogyo Kabushiki Kaisha, Osaka, Japan

[21] Appl. No.: 462,345

[22] Filed: Jan. 2, 1990

Related U.S. Application Data

[63] Continuation of Ser. No. 870,531, Jun. 4, 1986, abandoned.

[30] Foreign Application Priority Data

Jun. 4, 1985 [JP] Japan ............................. 60-119761

[51] Int. Cl.$^5$ ..................... C12P 13/02; C12N 1/20
[52] U.S. Cl. ................... 435/129; 435/252.1; 435/244
[58] Field of Search ............. 435/129, 170, 252.1, 435/863, 843, 840, 872, 244

[56] References Cited

U.S. PATENT DOCUMENTS

| | | | |
|---|---|---|---|
| 4,001,081 | 1/1977 | Commeyras et al. | 195/29 |
| 4,248,968 | 2/1981 | Watanabe et al. | 435/822 |
| 4,629,700 | 12/1986 | Prevatt et al. | 435/128 |

FOREIGN PATENT DOCUMENTS

| | | |
|---|---|---|
| 0093782 | 5/1983 | European Pat. Off. |
| 0178106 | 4/1986 | European Pat. Off. |
| 0188316 | 7/1986 | European Pat. Off. |

OTHER PUBLICATIONS

Goodfellow et al. "The Biology of the Actiomycetes" 1984, Academic Press.
Kawakami et al, Chem. Abstracts, vol. 107, 132672h, p. 587 (1987).
D. B. Harper, "Biochem. J.", 165, pp. 209–319 (1977).
Mr. Kuwahara et al, "J. Ferment. Technol.", vol. 58, No. 6, pp. 573–577 (1980).
Y. Asano et al, "Agric. Biol. Chem.", 44(10) pp. 2497–2498 (1980).
H. G. rast et al, "FEMS Microbiology Letters", 7, pp. 1–6 (1980).
M. J. Digeronimo et al, "Applied and Environmental Microbiology", vol. 31, pp. 900–906 (Jun. 1976), No. 6.
J. M. Miller et al, "J. of General Microbiology", 128, pp. 1803–1809 (1982).
Chem. Abstracts, vol. 96, 214058f.
Chem. Abstracts, vol. 97, 123589j.

*Primary Examiner*—Irene Marx
*Attorney, Agent, or Firm*—Birch, Stewart, Kolasch & Birch

[57] ABSTRACT

The present invention relates to a method of producing an amide which comprises subjecting a nitrile to the action of a microorganism belonging to the genus Rhodococcus and having the ability to hydrate the nitrile, and isolating the resulting amide. The microorganism is highly active to a wide variety of nitriles even at low temperatures and, in addition, the hydration reaction of nitriles has a high selectivity for the corresponding amides. Accordingly, this method ensures the production of amides in high yield without formation of by-products such as corresponding carboxylic acids.

1 Claim, No Drawings

METHOD OF PRODUCING AN AMIDE UTILIZING A MICROORGANISM

This application is a continuation of application Ser. No. 06/870,531 filed on Jun. 4, 1986, now abandoned.

This invention relates to a method of producing an amide utilizing a microorganism. More particularly, the present invention is concerned with a method of producing an amide in which a nitrile is hydrated by the action of a microorganism belonging to the genus Rhodococcus to obtain the corresponding amide and the amide is isolated. The method is advantageous in productivity and because a variety of amides can be produced from the corresponding nitriles.

Acrylamide and methacrylamide are known as the amides which are most important in the industrial field. Acrylamide is utilized as a polymer aggregating agent, a paper reinforcing agent, a fiber improving material or the like. Further, important utilization is being developed in the field of petroleum product recovery. On the other hand, methacrylamide is widely utilized as an ingredient of a coating composition, adhesive, photocrosslinkable composition or the like since it has a well-balanced characteristic with respect to hydrophilicity and hydrophobicity as well as excellent heat resistance and photocrosslinkability.

Known in the art is a process for producing an amide in which a nitrile is hydrated by using reduced copper as a catalyst. This process is disadvantageous in that regeneration of the catalyst is difficult and that isolation and purification of the amide produced need laborious procedures. Hence, it has been desired to develop a novel process which can be advantageously used in the industrial field.

In line with this effort for development of a novel and advantageous process, several proposals have recently been made which concern a process using a microorganism. For example, in U.S. Pat. No. 4,001,081 (corresponding to British Patent No. 1,535,307 and Japanese Patent Application Laid-Open Specification No. 51-86186/1976), it is proposed to produce an amide by treating a nitrile with a microorganism belonging to a member selected from the group consisting of the genera Bacillus, Bacteridium, Micrococcus and Brevibacterium. In U.S. Pat. No. 4,248,968 (corresponding to British Patent No. 2,018,240 and Japanese Patent Application Publication No. 56-17918/1981), it is proposed to produce an amide by treating a nitrile with a microorganism belonging to the genus Corynebacterium or Nocardia. In European Patent Application Laid-open Specification No. 0 093 782 (corresponding to Japanese Patent Application Publication No. 59-37951/1984), it is proposed to produce an amide by treating a nitrile with a microorganism belonging to the genus Pseudomonas. However, all of the above-mentioned microorganisms do not have a desirably high activity to convert a nitrile to the corresponding amide. Further, the proposed processes using the above-mentioned microorganisms, in most cases, have a drawback such that the amount of organic acids formed as by-products is not on a level that is allowable from the viewpoint of industrial production. Therefore, there is still a strong demand in the art for a novel process for producing an amide which is free from the abovementioned drawbacks of the prior art.

The inventors have made extensive and intensive studies to find and isolate a microorganism which has a desirably high activity to specifically convert a nitrile to the corresponding amide. As a result, it has unexpectedly been found that a microorganism belonging to the genus Rhodococcus is extremely effective for this purpose. Based on this unexpected finding, the present invention has been completed.

It is, therefore, an object of the present invention to provide a novel biological method of producing an amide from a nitrile efficiently and in high yield without formation of by-products. The foregoing and other objects, features and advantages of the present invention will be apparent to those skilled in the art from the following detailed description and appended claims.

According to the present invention, there is provided a method of producing an amide which comprises the steps of:

(1) subjecting a nitrile in an aqueous medium to the action of a microorganism, said microorganism belonging to the genus Rhodococcus and having the ability to hydrate the nitrile, thereby to converting the nitrile to the corresponding amide; and (2) isolating the amide from the aqueous medium.

In the method of the present invention, a nitrile is subjected to the action of a microorganism belonging to the genus Rhodococcus and having the ability to hydrate the nitrile. The above-mentioned microorganism is highly active to a wide variety of nitriles as set out hereinbelow even at low temperatures, for example at about 10° C. Due to the high activity of the microorganism at low temperatures, the method of the present invention can be conducted at low temperatures so that the microorganism can be used for a prolonged period of time.

It has been found that *Rhodococcus erythropolis*, especially the strain designated as *Rhodococcus erythropolis* AK-3132, is useful as the above-mentioned microorganism to attain the objects of the present invention, and that also the strains designated as *Rhodococcus* sp. AK-32 and *Rhodococcus* sp. AK-33 are useful as the above-mentioned microorganism to attain the objects of the present invention.

The microorganism strains *Rhodococcus* sp. AK-32, *Rhodococcus* sp. AK-33 and *Rhodococcus erythropolis* AK-3132 to be employed in the present invention have been deposited with the Fermentation Research Institute of the Agency of Industrial Science and Technology and assigned Accession Nos. FERM BP-1046, FERM BP-1047 and FERM BP-1040, respectively. These microorganism strains have the following bacteriological and chemotaxonomic properties.

| A: Rhodococcus sp. AK-32 | |
|---|---|
| (I) Bacteriological Properties | |
| (a) Morphology | |
| (1) Shape and Size of cells | rod 0.6–0.8 × 1.3–2.0 μm |
| (2) Polymorphism of cells | At the initial stage of culture, the cells are in a long bacillary form of rods, grow with branching and fragmentation, and later break and split into a coccoid or short bacillary form of rods. |
| (3) Motility | none |
| (4) Spore | none |
| (5) Gram staining | positive |
| (6) Acid fastness | negative |

-continued

(b) Growth State in Various Culture Mediums

| | | |
|---|---|---|
| (1) Bouillon agar plate culture | circular, opaque with luster, yellowish white | |
| (2) Bouillon agar slant agar | middle growth, surface smooth, with luster, yellowish white | |
| (3) Bouillon liquid culture | slow growth, slightly turbid, no precipitation | |
| (4) Bouillon gelatin stab culture | good growth on the surface, no liquefaction of gelatin | |
| (5) Litmus milk | no change | |

(c) Physiological Characteristics

| | | |
|---|---|---|
| (1) Reduction of nitrate | negative | |
| (2) Denitrification | negative | |
| (3) MR test | negative | |
| (4) VP test | negative | |
| (5) Formation of indole | negative | |
| (6) Formation of hydrogen sulfide | negative | |
| (7) Hydrolysis of starch | negative | |
| (8) Assimilation of citric acid | Simon's culture: positive | |
| (9) Assimilation of inorganic nitrogen source | Nitrate: positive Ammonium salt: positive | |
| (10) Formation of pigment | King-A culture: negative King-B culture: negative | |
| (11) Urease | positive | |
| (12) Oxidase | negative | |
| (13) Catalase | positive | |
| (14) Hydrolysis of cellulose | negative | |
| (15) Range for growth | ph 5–10 temperature 10–35° C. | |
| (16) Behavior to oxygen | aerobic | |
| (17) O-F test | negative | |
| (18) Heat resistance in 10% skim milk | 55° C./15 min: almost died 70° C./15 min: completely died | |
| (19) Formation of acid & gas from saccharide | Formation of acid | Formation of gas |
| L-Arabinose | − | − |
| D-Xylose | − | − |
| D-Glucose | + | − |
| D-Mannose | + | − |
| D-Fructose | − | − |
| Maltose | − | − |
| Sucrose | ± | − |
| Lactose | − | − |
| Trehalose | − | − |
| D-Sorbitol | + | − |
| D-Mannitol | + | − |
| Inositol | ± | − |

(II) Chemotaxonomic Properties

| | |
|---|---|
| (1) Kind of diaminopimelic acid of peptidoglycan forming cell wall | meso-diaminopimelic acid |
| (2) Kind of N-acyl group of peptidoglycan forming cell wall | glycolyl group |
| (3) GC (gas chromatography) pattern of somatic fatty acid | Straight-chain fatty acid having 16–18 carbon atoms is predominant. Characterized by presence of 10-methyloctadecanic acid. |
| (4) Mycolic acid | present, simple pattern |

B: Rhodococcus sp. AK-33

(I) Bacteriological Properties

(a) Morphology

| | |
|---|---|
| (1) Shape and size of cells | rod 0.5–0.6 × 1.6–2.8 μm |
| (2) Polymorphism of cells | At the initial stage of culture, the cells are in a long bacillary form of rods, grow with branching and fragmentation, and later break and split into a coccoid or short bacillary form of rods. |
| (3) Motility | none |
| (4) Spore | none |
| (5) Gram staining | positive |
| (6) Acid fastness | negative |

-continued

(b) Growth State in Various Culture Mediums

| | | |
|---|---|---|
| (1) Bouillon agar plate culture | circular, opaque with luster, yellowish white | |
| (2) Bouillon agar slant agar | middle growth, surface smooth, with luster, yellowish white | |
| (3) Bouillon liquid culture | slow growth, slightly turbid, forming precipitates | |
| (4) Bouillon gelatin stab culture | good growth on the surface, no liquefaction of gelatin | |
| (5) Litmus milk | no change | |

(c) Physiological Characteristics

| | | |
|---|---|---|
| (1) Reduction of nitrate | negative | |
| (2) Denitrification | negative | |
| (3) MR test | negative | |
| (4) VP test | negative | |
| (5) Formation of indole | negative | |
| (6) Formation of hydrogen sulfide | negative | |
| (7) Hydrolysis of starch | negative | |
| (8) Assimilation of citric acid | Simon's culture: positive | |
| (9) Assmilation of inorganic nitrogen source | Nitrate: positive Ammonium salt: positive | |
| (10) Formation of pigment | King-A culture: negative King-B culture: negative | |
| (11) Urease | positive | |
| (12) Oxidase | negative | |
| (13) Catalase | positive | |
| (14) Hydrolysis of cellulose | negative | |
| (15) Range for growth | pH 5–11 temperature 10–38° C. | |
| (16) Behavior to oxygen | aerobic | |
| (17) O-F test | oxidized | |
| (18) Heat resistance in 10% skim milk | 55° C./15 min: almost died 70° C./15 min: completely died | |
| (19) Formation of acid & gas from saccharide | Formation of acid | Formation of gas |
| L-Arabinose | − | − |
| D-Xylose | − | − |
| D-Glucose | − | − |
| D-Mannose | − | − |
| D-Fructose | − | − |
| Maltose | − | − |
| Sucrose | − | − |
| Lactose | − | − |
| Trehalose | − | − |
| D-Sorbitol | − | − |
| D-Mannitol | + | − |
| Inositol | ± | − |

(II) Chemotaxonomic Properties

| | |
|---|---|
| (1) Kind of diaminopimelic acid of peptidoglycan forming cell wall | meso-diaminopimelic acid |
| (2) Kind of N-acyl group of peptidoglycan forming cell wall | glycolyl group |
| (3) GC pattern of somatic fatty acid | Straight-chain fatty acid having 16–18 carbon atoms is predominant. Characterized by presence of 10-methyloctadecanic acid. |
| (4) Mycolic acid | present, simple pattern |

C: *Rhodococcus erythropolis* AK-3132

(I) Bacteriological Properties

(a) Morphology

| | |
|---|---|
| (1) Shape and size of cells | rod 0.5–0.8 × 1.5–2.7 μm |
| (2) Polymorphism of cells | At the initial stage of culture, the cells are in a long bacillary form of rods, grow with branching and fragmentation, and later break and split into a coccoid or short bacillary form of rods. |
| (3) Motility | none |
| (4) Spore | none |
| (5) Gram staining | positive |
| (6) Acid fastness | negative |

-continued

| (b) Growth State in Various Culture Mediums | |
|---|---|
| (1) Bouillon agar plate culture | circular, opaque with luster, yellowish white |
| (2) Bouillon agar slant agar | middle growth, surface smooth, with luster, yellowish white |
| (3) Bouillon liquid culture | slow growth, slightly turbid, no precipitation |
| (4) Bouillon gelatin stab culture | good growth on the surface, no liquefaction of gelatin |
| (5) Litmus milk | no change |
| (c) Physiological Characteristics | |
| (1) Reduction of nitrate | negative |
| (2) Denitrification | negative |
| (3) MR test | negative |
| (4) VP test | negative |
| (5) Formation of indole | negative |
| (6) Formation of hydrogen sulfide | negative |
| (7) Hydrolysis of starch | negative |
| (8) Assimilation of citric acid | Simon's culture: positive |
| (9) Assimilation of inorganic nitrogen source | Nitrate: positive Ammonium salt: positive |
| (10) Formation of pigment | King-A culture: negative King-B culture: negative |
| (11) Urease | positive |
| (12) Oxidase | negative |
| (13) Catalase | positive |
| (14) Hydrolysis of cellulose | negative |
| (15) Range for growth | pH 5-10 temperature 10-35° C. |
| (16) Behavior to oxygen | aerobic |
| (17) O-F test | — |
| (18) Heat resistance in 10% skim milk | 55° C./15 min: almost died 70° C./15 min: completely died |

| (19) Formation of acid & gas from saccharide | Formation of acid | Formation of gas |
|---|---|---|
| L-Arabinose | — | — |
| D-Xylose | — | — |
| D-Glucose | — | — |
| D-Mannose | — | — |
| D-Fructose | + | — |
| Maltose | + | — |
| Sucrose | — | — |
| Lactose | — | — |
| Trehalose | — | — |
| D-Sorbitol | + | — |
| D-Mannitol | + | — |
| Inositol | ± | — |

| (II) Chemotaxonomic Properties | |
|---|---|
| (1) Kind of diaminopimelic acid of peptidoglycan forming cell wall | meso-diaminopimelic acid |
| (2) Kind of N-acyl group of peptidoglycan forming cell wall | glycolyl group |
| (3) GC pattern of somatic fatty acid | Straight-chain fatty acid having 16-18 carbon atoms is predominant. Characterized by presence of 10-methyloctadecanic acid. |
| (4) Mycolic acid | present, simple pattern |

As a result of comparison of the foregoing bacteriological and chemotaxonomic properties to the descritpions in Bergey's Manual of Determinative Bacteriology (eighth edition 1974) and in The Prokaryotes, A Handbook on Habitats, Isolation, and Identificaiton of Bacteria (1981), it is noted that the strains Rhodococcus sp. AK-32, Rhodococcus sp. AK-33 and *Rhodococcus erythropolis* AK-3132 are aerobic, gram-positive rods having no motility. Further, it is noted that they are in a long bacillary form of rods but not in a hypha form and they grow with branching and fragmentation, and later break and split into a coccoid or short bacillary form of rods. The peptidoglycan of their cell walls has a meso-diaminopimelic acid, and the N-acyl group thereof is of glycolyl type. The GC analysis of their somatic fatty acids shows the predominance of straight-chain fatty acids and the presence of mycolic acid along with the characteristic existence of 10-methyloctadecanic acid. Therefore, it is apparent that these strains belong to the genus Rhodococcus. Differences are observed between these strains in growth conditions and acid formation from saccharide.

As the suitable nitriles to be subjected to the action of a microorganism, there may be mentioned, for example, saturated aliphatic nitriles such as acetonitrile, propionitrile, succinonitrile and adiponitrile, ethylenically unsaturated nitriles such as acrylonitrile and methacrylonitrile, aromatic nitriles such as benzonitrile and phthalodinitrile and heterocyclic nitriles such as nicotinonitrile.

The microorganism belonging to the genus Rhodococcus and having the ability to hydrate nitriles may be incubated in, for example, a culture medium containing, as a carbon and nitrogen source, a nitrile such as propionitrile, isobutylonitrile, methacrylonitrile or the like. However, the microorganism may preferably be incubated in a culture medium which contains, besides a nitrile as a carbon and nitrogen source, a carbon source such as glucose, aldose or the like, a nitrogen source such as ammonium sulfate, ammonium nitrate or the like and an organic nutrient source such as an yeast extract, malt extract, pepton, meat extract or the like. To this medium, an inorganic nutrient source such as a phosphate, sodium, potassium, iron, magnesium, manganese, zinc or the like may optionally be added. The pH value of the culture medium may be generally in the range of from 5 to 9, preferably in the range of from 6 to 8. The culturing temperature may be generally in the range of from 20° to 35° C., preferably in the range of from 27° to 32° C. Under these conditions, the culturing may be carried out aerobically for 2 to 5 days.

According to the method of the present invention, a nitrile in an aqueous medium is subjected to the action of a microorganism belonging to the genus Rhodococcus and having the ability to hydrate the nitrile. In practicing the method of the present invention, various modes are possible. For example, there can be mentioned a mode in which the microorganism is incubated in the presence of a nitrile to be hydrated and another mode in which a nitrile is brought into contact with the culture containing the incubated cells of the microorganism or with the cells of the microorganism harvested from the culture. There can also be mentioned a further mode in which a nitrile is contacted with the cells obtained by disrupting the collected microorganism. Moreover, there is still a further mode in which the cells of the microorganism are fixed onto a carrier and then they are brought into contact with a nitrile. The abovementioned harvest of cells may be carried out by centrifugation or other known technique, and the disruption of cells may be effected mechanically e.g. by means of a homogenizer, or by supersonic vibration.

In the present invention, the culture containing incubated cells as it is may be brought into contact with a nitrile, as mentioned above. Alternatively, the cells harvested from the culture may be dispersed in water or a buffer such as phosphate buffer (for example, pH 7-9), and contacted with a nitrile, thereby causing the nitrile to be hydrated rapidly to form the corresponding amide. In the present invention, the conditions for hydrating nitriles are not critical. In general, the method of the present invention may be practiced as follows. An aqueous the microorganism and 0.2 to 10 % by weight of a nitrile, which suspension has a pH value of 5 to 10, is prepared, and the suspension is maintained at 0 to 30° C. for a period of about .2 minutes to about 8 hours to hydrate the nitrile. In this connection, it is noted that the nitrile to be used in the present invention generally exhibits a high toxicity to the organism. In view of this, it is preferred that the concentration of the nitrile in the reaction medium be controlled within a level, for example 2% by weight or less, which does not adversely affect the hydration reaction. Therefore, as a preferred method, there may be mentioned a method in which the nitrile is gradually added continuously or intermittently in the course of the hydration reaction so that the deactivation of the microorganism can be prevented. In this connection, it is noted that lowering of the temperature of the reaction medium is also effective to retain the activity of the microorganism for a prolonged period of time.

From the resulting reaction mixture, the amide produced may be isolated by means of customary techniques such as centrifugation, membrane separation, vacuum concentration, crystalization, etc., thereby obtaining a purified amide. According to need, coloring substances, impurities and the like may be removed, before the vacuum concentration, crystalization or the like, by a treatment using activated charcoal, ion exchange resin or the like.

According to the method of the present invention in which use is made of a microorganism belonging to the genus Rhodococcus and having the ability to hydrate a nitrile, an amide can be produced at a low cost on a commercial scale. Due to the high activity of the above-mentioned microorganism and high selectivity of the hydration reaction of nitriles for the corresponding amides, various amides can be produced with a conversion ratio of almost 100%, i.e. with an extremely small amount of or without formation of by-products. Further, owing to the high activity of the microorganism even at low temperatures, the hydration of a nitrile can be carried out at low temperatures, so that the microorganism can be used for a prolonged period of time.

The present invention will now be explained in more detail with reference to the following Examples but they should not be construed as limiting the scope of the present invention.

EXAMPLE 1

(1) Culture
Rhodococcus sp. AK-32 was cultured under the following conditions.

| 1) Culture Medium: | |
|---|---|
| Trypton | 1.7 wt % |
| Soy peptone | 0.3 wt % |
| Glucose | 0.25 wt % |
| Isobutyronitrile | 0.5 wt % |
| NaCl | 0.5 wt % |
| K$_2$HPO$_4$ | 0.25 wt % |
| pH | 7.3 |

2) Cultural Conditions: 30° C./4 days
(2) Hydration of Methacrylonitrile
The cells in the cultured broth thus obtained were collected by centrifugation, washed with physiological saline and used for the hydration as follows. 0.2 Part by weight (on a dry basis) of the cells, 2.0 parts by weight of methacrylonitrile and 97.8 parts by weight of 0.05 M phosphate buffer (pH 7.0) were mixed to prepare a reaction mixture. The temperature of the reaction mixture was maintained at 30° C. Five minutes later, the reaction mixture was analyzed by gas chromatography. As a result, it was found that 2.5 parts by weight of methacrylamide were contained in the reaction mixture, and that the methacrylonitrile remaining unreacted and by-product such as methacrylic acid or the like were not found in the reaction mixture. This shows that the methacrylonitrile was hydrated almost quantitatively to methacrylamide and the reaction was completed.

COMPARATIVE EXAMPLE 1

(1) Culture
Corynebacterium sp. N-774 (Fermentation Research Institute Accession No. 4446) was incubated under the following conditions.

| 1) Culture Medium: | |
|---|---|
| Glucose | 1.0 wt % |
| Peptone | 0.5 wt % |
| Yeast extract | 0.3 wt % |
| Malt extract | 0.3 wt % |
| pH | 7.2 |

2) Culture Conditions: 28° C./3 days
(2) Hydration of methacrylonitrile
After incubation, the cultured broth was subjected to centrifugation to separate the cells from the cultured broth. The thus obtained cells were washed with water and then dried. 3 Parts of the dried cells were mixed with 97 parts of water. Then, methacrylonitrile was added dropwise to the resulting mixture maintained at 30° C. at a rate of 3 parts per hour under stirring while controlling the pH at 8.5 using potassium hydroxide, to effect hydration reaction. After the reaction for 4 hours, the addition of methacrylonitrile was stopped, but the stirring was continued for further 30 min to complete the reaction. After completion of the reaction, the reaction mixture was centrifuged to remove the cells. Thus, there was obtained a clear solution. The content of methacrylamide in the solution was determined by liquid chromatography and found to be 13.0 wt %, which means that the yield is 95 mole %.

EXAMPLE 2

(1) Culture
Rhodococcus sp. AK-32 was cultured under the following conditions.

| 1) Culture Medium: | |
|---|---|
| Glucose | 1.0 wt % |
| Meat extract | 1.0 wt % |
| Peptone | 1.0 wt % |
| Isobutyronitrile | 0.25 wt % |
| NaCl | 0.1 wt % |
| KH$_2$PO$_4$ | 0.1 wt % |
| MgSO$_4$.7H$_2$O | 0.05 wt % |
| FeSO$_4$.7H$_2$O | 0.005 wt % |
| MnSO$_4$.4~5H$_2$O | 0.005 wt % |
| (NH$_4$)$_2$SO$_4$ | 0.1 wt % |
| KNO$_3$ | 0.1 wt % |
| pH | 7.0 |

2) Culturing Conditions: 30° C./3 days
(2) Hydration of Nitriles

The cells of the microorganism were collected in substantially the same manner as in Example 1.

Using various nitriles, the hydration of the nitriles was carried out under the following conditions.

| | |
|---|---|
| Cell (on a dry basis) | 0.2 wt % |
| Substrate nitrile | 2.0 wt % |
| 0.05M phosphate buffer (pH 7.0) | 97.8 wt % |
| Temperature | 10° C. |
| Reaction time | 5 minutes |

The results obtained are shown below.

| Test Nitrile | Amide-forming activity*1 (mol/g · hr) | Acid-forming ratio*2 (%) |
|---|---|---|
| Acetonitrile | 0.29 | 0.10 |
| Propionitrile | 1.99 | 0.12 |
| Acrylonitrile | 1.98 | 0.05 |
| Isobutyronitrile | 1.22 | 0.10 |
| Methacrylonitrile | 0.95 | 0.02 |
| Succinonitrile | 1.50 | below 0.1 |
| Adiponitrile | 0.84 | below 0.1 |
| Benzonitrile | 0.10 | below 0.1 |
| Terephthalonitrile | 0.96 | below 0.1 |
| Nicotinonitrile | 0.02 | below 0.1 |

(Note)

$$*1. \frac{\text{Amount of produced amide (mol)}}{\text{Amount of dry cell (g)} \times \text{Reaction time (hr)}}$$

$$*2. \frac{\text{Amount of formed carboxylic acid (mol)}}{\text{Amount of nitrile added (mol)}} \times 100$$

The above-mentioned amounts were determined by gas chromatography, except for the amounts of amides having a high boiling point as those obtained from succinonitrile, adiponitrile, benzonitrile, terephthalonitrile and nicotinonitrile. The amounts of these amides were determined by liquid chromatography.

EXAMPLE 3

(1) Culture

Rhodococcus sp. AK-33 was cultured under substantially the same conditions as in Example 2.

(2) Hydration of Acrylonitrile

Cells of the microorganism were collected from the cultured broth obtained in substantially the same manner as in Example 1. To 1 l of 0.05 M phosphate buffer (pH 7.0) were added the cells in an amount of 10 g (on a dry basis) to prepare a dormant cell dispersion. At intervals of 20 minutes, acrylonitrile was added to the dispersion in an amount of 20 g at a temperature of 2° to 3° C. Just before every addition of acrylonitrile, the concentrations of acrylonitrile and acrylamide in the reaction mixture were determined by gas chromatography. From the results, it was found that the amount of the produced acrylamide increased linearly with the lapse of reaction time until 5 hours after the initiation of the hydration reaction, and 450 g/l-buffer of acrylamide was produced. At that time, the hydration reaction was still be able to proceed further but the reaction rate was lowered and, therefore, the reaction was terminated.

The yield of acrylamide was about 100 mole %, and the quantity of acrylic acid formed as a by-product was only about 0.1% based on the acrylonitrile added.

COMPARATIVE EXAMPLE 2

(1) Culture

Pseudomonas chlororaphis B-23 (Fermentation Research Institute Accession No. 187) was cultured under the following conditions.

| 1) Culture Medium: | |
|---|---|
| Dextrin | 0.5 wt % |
| K2HPO4 | 0.2 wt % |
| MgSO4.7H2O | 0.02 wt % |
| Isobutyronitrile | 0.2 wt % |
| NaCl | 0.1 wt % |
| pH | 7.0 |

2) Culturing Conditions: 28° C./3 days (2) Hydration of Acrylonitrile

The cells of the microorganism were separated from the cultured broth and washed with water. The thus obtained cells were dispersed in phosphate buffer (pH 7.0) at a concentration of 20 g (on a dry basis)/l-buffer to prepare a dormant cell dispersion. To the dispersion, acrylonitrile was intermittently added at a temperature of 0° to 4° C. so that the concentration of acrylonitrile was maintained at 0.4 M. The amount of the produced acrylamide increased linearly with the reaction time, and 7.5 buffer of acrylamide was produced. The reaction seemed to proceed further but was terminated at this stage since the reaction mixture became viscous.

The yield of acrylamide was about 99 mole %, and the quantity of acrylic acid formed as a by-product was about 0.7 % based on the acrylonitrile added.

EXAMPLE 4

(1) Culture

Rhodococcus sp. AK-32 was cultured in substantially the same manner as in Example 2.

(2) Hydration of Methacrylonitrile

The cells were collected in substantially the same manner as in Example 3. To 1% of 0.05M phosphate buffer (pH 7.0) were added 5 g (on a dry basis) of the cells to prepare a dormant cell dispersion. Methacrylonitrile was added to the dispersion at intervals of one hour in an amount of 20 g at a temperature of 2° to 3° C. Just before every addition of methacrylonitrile, the concentration of methacrylonitrile remaining unreacted in the reaction mixture was determined by gas chromatography. About 5 hours after the initiation of the addition, methacrylamide began to separate out as crystals. Thereafter, the addition of methacrylonitrile was continued at a decreased rate of 20 g per 2 hours because the reaction rate was lowered to cause some methacrylonitrile to be left unreacted. The hydration reaction was continued for 25 hours. As a result, 245 g of methacrylamide crystals were obtained. The reaction mixture was kept refrigerated at 4° C. for 1,600 hours. Then, 20 g of methacrylonitrile was added to the mixture to effect a further hydration reaction at 2° to 3 ° C. 2 hours later, no unreacted methacrylonitrile was detected. The yield of methacrylamide was about 100 mole %, and the quantity of methacrylic acid formed as a by-product was as little as about 0.1% based on the methacrylonitrile added.

EXAMPLE 5

(1) Culture

Rhodococcus sp. AK-32 was cultured in substantially the same manner as in Example 2.

(2) Hydration of Methacrylonitrile

The cells were collected in substantially the same manner as in Example 3. The cells were fixed to calcium alginate gels to obtain immobilized cells. 25 g of the immobilized cells (0.5 g cells, on a dry basis) were added to 75 g of 0.5 weight % aqueous solution of calcium chloride (pH 7.0) to prepare a dispersion of immobilized dormant cells. Methacrylonitrile was added to the dispersion at intervals of one hour in an amount of 2 g at a temperature of 2 to 3° C. Just before every addition of methacrylonitrile, the concentration of methacrylonitrile remaining unreacted in the reaction mixture was determined by gas chromatography. About 5 hours after the initiation of the addition, methacrylamide began to separate out as crystals. Thereafter, the addition of methacrylonitrile was continued at a decreased rate of 2 g per 2 hours because the reaction rate was lowered to cause some methacrylonitrile to be left unreacted. The hydration reaction was continued for 15 hours. As a result, 10.8 g of methacrylamide crystals were obtained. The quantity of methacrylic acid formed as a by-product was as little as about 0.3% based on the methacrylonitrile added.

EXAMPLE 6

(1) Culture

Rhodococcus erythropolis AK-3132 was cultured under the following conditions.

| 1) | Culture Medium: | |
|---|---|---|
| | Isobutyronitrile | 0.5 wt % |
| | KH$_2$PO$_4$ | 0.1 wt % |
| | MgSO$_4$.7H$_2$O | 0.05 wt % |
| | FeSO$_4$.7H$_2$O | 0.005 wt % |
| | MnSO$_4$.4~5H$_2$O | 0.005 wt % |
| | (NH$_4$)$_2$SO$_4$ | 0.1 wt % |
| | KNO$_3$ | 0.1 wt % |
| | pH | 7.0 |

2) Culture Conditions: 30° C./5 days (2) Hydration of Methacrylonitrile

The cells were collected from the cultured broth thus obtained in substantially the same manner as in Example 1. 1.0 part by weight (on a dry basis) of the cells, 1.0 part by weight of methacrylonitrile and 98.0 parts by weight of 0.05M phosphate buffer (pH 7.0) were mixed to prepare a reaction mixture. The reaction mixture was maintained at a temperature of 30° C. 30 minutes later, the reaction mixture was analyzed by gas chromatography. As a result, it was found that by the reaction for 30 minutes there was formed methacrylamide in an amount of 0.1 wt % based on the reaction mixture, and all of the methacrylonitrile which was not converted to methacrylamide remained unreacted in the reaction mixture.

EXAMPLE 7

The culture medium described in Example 2 was put into each of two 500 ml conical flasks in an amount of 20 g. In the medium, the strain Rhodococcus sp. AK was incubated under agitation using a rotary shaker at 220 rpm at 30° C. for 24 hours. Then, the incubation in one of the two flasks was stopped to determine the cell concentration. As a result, it was found that the cells were present at a concentration of 1050 ppm. To the other flask was added methacrylonitrile at a rate of 0.25 g per hour and incubation was conducted under the above-mentioned conditions. The incubation was stopped 72 hours after the initiation of the incubation to determine the concentration of the cells and the amount of methacrylamide produced in the flask. The amount of methacrylamide was determined by gas chromatography. It was found that the cell concentration increased to 5,100 ppm, and that the methacrylamide produced in the flask was 11.2 g. In the culture medium, no methacrylic acid was detected whereas 500 ppm of methacrylonitrile was found to remain unreacted.

EXAMPLE 8

Rhodococcus sp. AK-32 was cultured under substantially the same conditions as in Example 2. Then, 20 g of the cultured broth containing the cells was put into a 50 ml conical flask in which a magnetic rotor was placed. The flask was put in a water bath maintained at a temperature of 4° C. The cultured broth was stirred for 2 hours. Thereafter, methacrylonitrile was added to the cultured broth at a rate of 0.4 g per hour. 8 Hours after the initiation of addition of methacrylonitrile, methacrylamide began to separate out as crystals. The addition of methacrylonitrile was further continued. 18 Hours after the initiation of addition of methacrylonitrile, it became impossible to rotate the magnetic rotor because a large amount of precipitated crystals accumulated in the flask. So the addition of methacrylonitrile was stopped. The resulting slurry in the flask was diluted with water to 1000 g, thereby to dissolving the methacrylamide crystals in the water. The methacrylamide concentration of the solution was determined by gas chromatography to be 0.91 wt %. Neither methacrylonitrile nor methacrylic acid was detected in the reaction mixture.

EXAMPLE 9

Rhodococcus sp. AK-32 was cultured in substantially the same manner as in Example 2. The culture broth thus obtained was subjected to centrifugation to collect cells. The collected cells were washed with an aqueous solution of potassium chloride (0.05 M, pH 7.0) and subjected to further centrifugation. To 2 g of the thus obtained dormant cells of strain AK-32 (water content, 80%) was added 40 g of 0.05 M phosphate buffer (pH 7.0) to prepare a dormant cell dispersion. The dispersion was treated by means of a homogenizer for 30 min while maintaining the temperature at 0° to 5° C., thereby to disrupting the cells. To 98 parts by weight of the thus treated dispersion containing the disrupted cells was added 2.0 parts by weight of methacrylonitrile to effect the hydration thereof at 30° C. in substantially the same manner as in Example 1. 10 minutes after the initiation of the hydration reaction, the reaction mixture was analyzed. As a result, the formation of 2.5 wt % based on the reaction mixture (yield: 100 mole %) of methacrylamide was confirmed.

What is claimed is:

1. A method for the production of an amide from a nitrile which comprises:
    (1) culturing a microorganism selected from the group consisting of Rhodococcus sp. A-32, FERM BP-1046, and Rhodococcus sp. A-33, FERM BP-1047, in an aqueous nutrient medium containing assimilable sources of carbon, nitrogen, inorganic substances and 0.25 to 0.5 percent by weight of an inducer nitrile selected from the group consisting of propionitrile, isobutyronitrile and methacrylonitrile;
    (2) contacting in an aqueous medium said cultured microorganism with a second nitrile to thereby convert said second nitrile to the corresponding amide;
    (3) isolating said amide from the aqueous medium; with the proviso that when said microorganism is Rhodococcus sp. A-32, FERM BP-1046, said second nitrile is selected from the group consisting of acetonitrile, propionitrile, acrylonitrile, isobutyronitrile, methacrylonitrile, succinonitrile, adiponitrile, benzonitrile and terephthalonitrile and when said microorgnaism is Rhodococcus sp. A-33, FERM BP-1047 said second nitrile is acrylonitrile or methacrylonitrile.

* * * * *